United States Patent
Sim et al.

(10) Patent No.: US 8,459,299 B2
(45) Date of Patent: Jun. 11, 2013

(54) FLUID CONTROL APPARATUS

(75) Inventors: Tae-seok Sim, Seoul (KR); Chin-sung Park, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 692 days.

(21) Appl. No.: 12/555,120

(22) Filed: Sep. 8, 2009

(65) Prior Publication Data

US 2010/0229979 A1  Sep. 16, 2010

(30) Foreign Application Priority Data

Mar. 16, 2009  (KR) .................. 10-2009-0022182

(51) Int. Cl.
   *F04F 3/00* (2006.01)
(52) U.S. Cl.
   USPC .............................. 137/565.33; 137/565.23
(58) Field of Classification Search
   USPC ............ 137/565.17, 565.23, 565.29, 565.33, 137/599.03, 599.08, 599.09, 601.14, 565.37
   See application file for complete search history.

(56) References Cited

U.S. PATENT DOCUMENTS

| | | | | |
|---|---|---|---|---|
| 2,945,445 A | * | 7/1960 | Smith et al. | 417/7 |
| 5,098,580 A | * | 3/1992 | Andersen | 210/745 |
| 5,433,238 A | * | 7/1995 | Cannizzaro et al. | 137/14 |
| 6,772,784 B1 | | 8/2004 | Jones et al. | |
| 6,787,111 B2 | | 9/2004 | Roach et al. | |
| 7,934,519 B2 | * | 5/2011 | Zantl | 137/563 |
| 2002/0076806 A1 | | 6/2002 | Van Gelder | |
| 2003/0198576 A1 | | 10/2003 | Coyne et al. | |
| 2004/0092033 A1 | | 5/2004 | Gustafson et al. | |
| 2004/0209354 A1 | * | 10/2004 | Mathies et al. | 435/287.2 |
| 2006/0012784 A1 | | 1/2006 | Ulmer | |
| 2007/0146238 A1 | * | 6/2007 | Fork | 345/55 |
| 2007/0231880 A1 | | 10/2007 | Chang-Yen et al. | |
| 2008/0187445 A1 | | 8/2008 | Gale et al. | |
| 2008/0314450 A1 | * | 12/2008 | Hawker et al. | 137/2 |

FOREIGN PATENT DOCUMENTS

| | | | |
|---|---|---|---|
| CN | 1908658 | * | 2/2007 |
| KR | 1020030059797 A | | 7/2003 |
| KR | 1020070050589 A | | 5/2007 |

OTHER PUBLICATIONS

Office Action in CN Application No. 201010109487.9 mailed on Feb. 1, 2013.

* cited by examiner

*Primary Examiner* — John Rivell
*Assistant Examiner* — Kevin Barss
(74) *Attorney, Agent, or Firm* — Leydig, Voit & Mayer, Ltd.

(57) ABSTRACT

A fluid control apparatus includes a fluid system, a pump and valve array, which selectively provides a pressure or a vacuum of various degrees, and an intermediate bin, which is connected between the pump and valve array and the fluid system, the intermediate bin including a reservoir unit, which stores a fluid discharged from the fluid system.

11 Claims, 2 Drawing Sheets

FIG. 3
|  | VALVE 1 | VALVE 2 | VALVE 3 |
|---|---|---|---|
| LOW PRESSURE | Off | On or Off | Off |
| HIGH PRESSURE | On | On or Off | Off |
| HIGH VACCUM | On or Off | Off | On |
| LOW VACCUM | On or Off | On | On |
FIG. 4
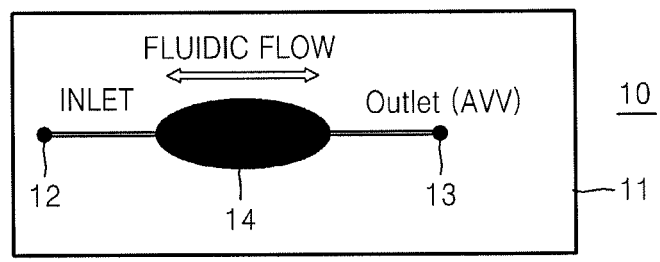
FIG. 5
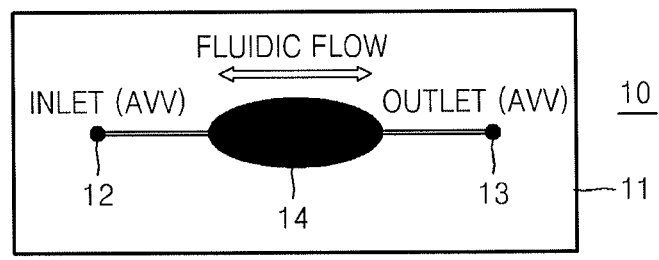

FLUID CONTROL APPARATUS

CROSS-REFERENCE TO RELATED APPLICATIONS

This application claims priority to Korean Patent Application No. 10-2009-0022182, filed on Mar. 16, 2009, and all the benefits accruing therefrom under 35 U.S.C. §119, the content of which in its entirety is herein incorporated by reference.

BACKGROUND

1. Field

One or more embodiments relate to a fluid control apparatus, and more particularly, to a fluid control apparatus capable of injecting, vacuuming and discharging gas using one port.

2. Description of the Related Art

A lab-on-a-chip ("LOC") is a device in which a plurality of laboratory functions are integrated, and is also referred to as a 'laboratory in a chip' or a 'laboratory on a chip'. A LOC includes a substrate formed of plastic, glass, silicon or the like, and a miniature reaction chamber, having a sub nano-liter volume, disposed on the substrate. By using the miniature reaction chamber and a very small amount of a sample, experiments or research processes usually performed in conventional laboratories at a larger scale may be quickly performed in the LOC. Due to this advantage, a LOC is regarded as a next generation diagnosis apparatus. By using a LOC, diagnosis of various cancers or measurement of red blood cells, leukocyte or cells may be conducted with only one drop of blood.

In order to conduct diagnosis using a LOC, a fluid control apparatus for providing a reagent and a sample needs to be included in the LOC. In general, there are various methods of driving a fluid in a fluid system. For example, a pump installed in a fluid system may be used, or a fluid may be moved using air pressure or vacuum applied from the outside. By applying air pressure or vacuum from the outside to control the movement of the fluid in the fluid system, an inlet port, through which the fluid is supplied to the fluid system, an outlet port for discharging the fluid and a vent or a waste for removing unnecessary solutions, are included. Also, according to the application, the fluid may be pushed by applying air pressure or pulled using a vacuum.

However, according to the above-described controlling method, the number of needed ports is increased. For example, the number of ports connected to the reaction chamber in the LOC is increased, and a fluid control unit is desirably connected to each port in order to control fluid flow via each of the ports. Accordingly, when an array including a large number of chambers is integrated in one LOC, the size of the fluid control apparatus increases geometrically according to the increase in the number of ports. In addition, as the number of ports increases, complexity of the interface between the LOC and the fluid control apparatus increases.

SUMMARY

One or more embodiments include a fluid control apparatus capable of injecting, vacuuming and discharging gas by using one port.

Additional aspects, features and advantages will be set forth in part in the description which follows.

To achieve the above and/or other aspects, features and advantages, one or more embodiments includes a fluid control apparatus for driving a fluid in a fluid system including: a pump and valve array, which selectively provides a pressure or a vacuum of various degrees; and an intermediate bin, which is connected between the pump and valve array and the fluid system, the intermediate bin including a reservoir unit, which stores a fluid discharged from the fluid system.

The pump and valve array may include: a pump system including a pressure unit, which provides an air pressure and a vacuum unit, which provides a vacuum; a plurality of regulators, which are separately connected to the pressure unit and the vacuum unit of the pump system and output the air pressure or the vacuum; and a valve system, which selects a regulator to output the air pressure or the vacuum.

The pump system may further include a pressure pump, which provides an air pressure, and a vacuum pump, which provides a vacuum.

The pump system may provide the air pressure and the vacuum at the same time.

The plurality of regulators may include: first and second regulators, which are connected to the pressure unit of the pump system and output a pressure of various degrees; and third and fourth regulators, which are connected to the vacuum unit of the pump system and output a vacuum of various degrees.

The valve system may include: a first valve, which is connected to the first and second regulators and selects a pressure of one of the first and second regulators; a second valve, which is connected to the third and fourth regulators and selects a vacuum of one of the third and fourth regulators; and a third valve, which is connected to one of the first and second valves and selects an output of the first and second valves.

The first through third valves may be solenoid valves.

One of the plurality of regulators may output a pressure equal to atmospheric pressure.

The intermediate bin may further include: a first through hole, which supplies pressure or vacuum from the pump and valve array to the reservoir unit; and a second through hole, which outputs the pressure or vacuum supplied to the reservoir unit to the outside.

The fluid control apparatus may further include a first tube connected between the pump and valve array and the first through hole, and a second tube connected between the second through hole and the fluid system.

If a vacuum is applied, a fluid supplied from the fluid system through the second through hole may be gathered in the reservoir unit.

The fluid system may include a lab-on-a-chip ("LOC").

In an embodiment, the first valve selects only a pressure of one of the first and second regulators; the second valve selects only a vacuum of one of the third and fourth regulators; and a third valve selects only one output of the first and second valves.

BRIEF DESCRIPTION OF THE DRAWINGS

These and/or other aspects, features and advantages will become more apparent and more readily appreciated from the following description of the embodiments, taken in conjunction with the accompanying drawings in which:

FIG. 3 is a table showing an exemplary embodiment of operational conditions of the pump and valve array illustrated in FIG. 2; and FIGS. 4 and 5 illustrate an exemplary embodiment in which a fluid flow is controlled in a fluid system using a fluid control apparatus.

DETAILED DESCRIPTION

Figure 1:
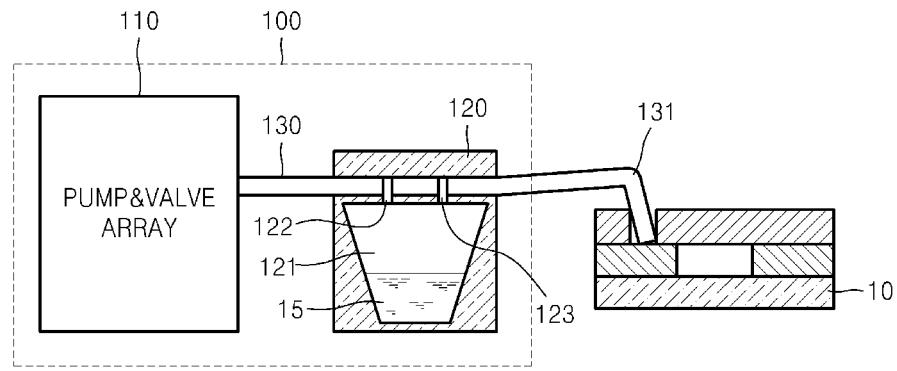
FIG. 1 is a schematic view illustrating an exemplary embodiment of a structure of a fluid system including a fluid control apparatus.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

FIG. 1 is a schematic view illustrating an exemplary embodiment of a structure of a system including a fluid control apparatus 100. Referring to FIG. 1, the fluid control apparatus 100, which supplies a fluid in a flow passage by using a port of the fluid system 10, is connected to the fluid system 10. For example, the fluid control apparatus 100 may push a fluid by applying a pressure to the fluid system 10 either via an inlet or an outlet of the fluid system 10 or may attract a fluid by applying a vacuum. In this respect, the fluid control apparatus 100 may be referred to as an air vacuum vent ("AVV") system.

Referring to FIG. 1, the fluid control apparatus 100 includes a pump and valve array 110, which selectively provides a pressure or a vacuum, and an intermediate bin 120, which is connected between the pump and valve array 110 and the fluid system 10. The intermediate bin 120 includes a reservoir unit 121 for storing a fluid 15 discharged from the fluid system 10. In addition, the intermediate bin 120 includes first and second through holes 122 and 123, respectively, connected to the reservoir unit 121 through inner walls of the intermediate bin 120. For example, the first and second through holes 122 and 123 may be connected to an upper portion of the reservoir unit 121 through lateral surfaces of the intermediate bin 120. The first through hole 122 provides a pressure or a vacuum supplied from the pump and valve array 110 to the reservoir unit 121, and the second through hole 123 may output the pressure or the vacuum supplied to the reservoir unit 121 to the outside, for example, to the fluid system 10.

Also, the fluid control apparatus 100 may further include a first tube 130 connected between the pump and valve array 110 and the first through hole 122, and a second tube 131 connected between the second through hole 123 and the outside, thus the second tube 131 may be connected between the second through hole 123 and the fluid system 10. Thus, the pressure and the vacuum output from the pump and valve array 110 may be supplied to the reservoir unit 121 through the first tube 130 and the first through hole 122 and be supplied to the fluid system 10 through the second through hole 123 and the second tube 131.

In an embodiment, since the intermediate bin 120, which includes the reservoir unit 121, is disposed between the pump and valve array 110 and the fluid system 10, when pulling a fluid in the fluid system 10 by applying a vacuum, a flow of the fluid 15 into the pump and valve array 110 is substantially reduced or effectively prevented. In other words, the fluid 15, which is discharged from the fluid system 10 and has passed through the second through hole 123, may gather in the reservoir unit 121 of the intermediate bin 120. Accordingly, the pump and valve array 110 may continuously apply a vacuum to the fluid system 10. In addition, a selected amount of fluid may be discharged from the fluid system 10, and thus, when applying a pressure to the fluid system 10 after applying a vacuum, an excess amount of fluid, if present, may be substantially reduced or effectively prevented from remaining in a path between the pump and valve array 110 and the fluid system 10. Thus, by disposing the intermediate bin 120, which includes the reservoir unit 121, between the pump and valve array 110 and the fluid system 10, the pump and valve array 110 may alternately and repeatedly supply a pressure and vacuum to the fluid system 10 without stopping. Accordingly, a fluid in the fluid system 10 may be controlled without restriction by using only one port, such as an inlet or an outlet.

Figure 2:
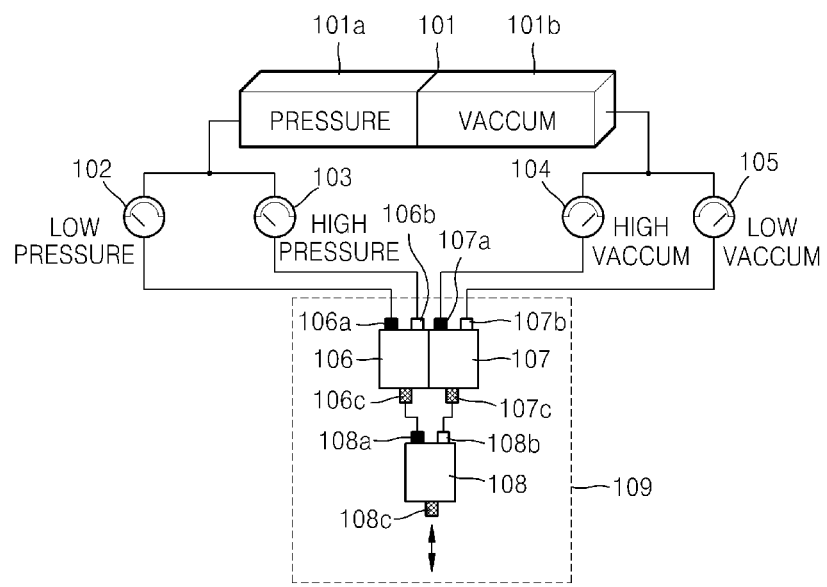
FIG. 2 is a schematic view illustrating an exemplary embodiment of a configuration of a pump and valve array of the fluid control apparatus of FIG. 1.

FIG. 2 is a schematic view illustrating an exemplary embodiment of a configuration of the pump and valve array 110 of the fluid control apparatus 100. Referring to FIG. 2, the pump and valve array 110 includes a pump system 101, including a pressure unit 101a providing a pressure and a vacuum unit 101b providing a vacuum, a plurality of regulators, including first to fourth regulators 102, 103, 104, and 105, respectively, which are respectively connected to the pressure unit 101a and the vacuum unit 101b of the pump system 101, and a valve system 109 including first, second and third valves 106, 107, and 108, respectively, which select one of the first to fourth regulators 102, 103, 104 or 105 to output a selected pressure or a selected vacuum. The first to fourth regulators 102, 103, 104 and 105, respectively, output a pressure or a vacuum and constantly maintain the output. To this end, the first to fourth regulators 102, 103, 104 and 105 may be set up in advance so that a selected amount of pressure or vacuum is output.

According to an embodiment, the pump system 101 may include a pump, which provides a pressure and a vacuum at the same time. In an embodiment, an output port for the pressure unit 101a and an output port for the vacuum port 101b may be provided in a pump. In an embodiment, one pump provides a pressure and a vacuum at the same time, thus an output port for the pressure unit 101a and an output port for the vacuum port 101b may be provided in one pump. For example, if the fluid system 10 is a miniaturized system such as a lab-on-a-chip ("LOC"), which does not need a large amount of pressure or vacuum, the pump system 101 may include only one pump. Alternatively, the pump system 101 may include both a pressure pump providing a pressure and a vacuum pump providing a vacuum. Thus in an embodiment, the pressure pump is the pressure unit 101a and the vacuum pump is the vacuum unit 101b. For example, if the fluid system 10 is a large-sized system, such as may be found in a factory, the pump system 101 may include both a pressure pump and a vacuum pump.

Also, as illustrated in FIG. 2, the first to fourth regulators 102, 103, 104 and 105 may include first and second regulators 102 and 103, which are connected to the pressure unit 101a of the pump system 101 and output varying degrees of pressure, respectively, and third and fourth regulators 104 and 105, which are connected to the vacuum unit 101b of the pump system 101 and output varying degrees of vacuum, respectively. For example, the first regulator 102 may change a pressure from the pump unit 101a to a lower pressure and output the pressure constantly, and the second regulator 103 may be set so as to change a pressure from the pressure unit 101a to a higher pressure and output the pressure constantly. The lower and higher pressures are relative to each other, and indicate that the pressure output from the second regulator 103 is higher than the pressure output from the first regulator 102. In the same manner, the third regulator 104 outputs a higher vacuum from the vacuum unit 101b, and the fourth regulator 105 may change a vacuum from the vacuum unit 101b to a lower vacuum and output the same. The higher vacuum and the lower vacuum are also relative to each other. For example, the third regulator 104 may maintain a vacuum state provided by the vacuum unit 101b to have a maximum vacuum, and the fourth regulator 105 may reduce the vacuum provided by the vacuum unit 101b and output the same.

In an embodiment, the valve array 109, including the first, second and third valves 106, 107 and 108, respectively, may include a first valve 106, which is connected to the first and second regulators 102 and 103 and selects a pressure of only one of the first and second regulators, a second valve 107, which is connected to the third and fourth regulators 104 and 105 and selects a vacuum of only one of the third and fourth regulators, and a third valve 108, which is connected to the first and second valves 106 and 107 and selects an output of only one of the first and second valves 106 and 107. For example, a first pressure input port 106a of the first valve 106 may be connected to the first regulator 102, and a second pressure input port 106b may be connected to the second regulator 103. Also, a first vacuum input port 107a of the second valve 107 may be connected to the third regulator 104, and a second vacuum input port 107b may be connected to the fourth regulator 105. A first valve input port 108a of the third valve 108 may be connected to a first output port 106c of the first valve 106, and a second valve input port 108b may be connected to a second output port 107c of the second valve 107.

Each of the first, second, and third valves 106, 107, and 108 may select one of the two inputs thereto and output the same according to an on/off state. For example, the first through third valves 106, 107, and 108 may be solenoid valves. For example, in an off state, the first, second, and third valves 106, 107, and 108 may output an input to the first pressure input port 106a, the first vacuum input port 107a, and the first valve input port 108a, to the first output port 106c, the second output port 107c, and the third output port 108c. In an on state, the first, second, and third valves 106, 107, and 108 may output an input to the second pressure input port 106b, the second vacuum input port 107b, and the second valve input port 108b, to the first to third output ports 106c, 107c, and 108c, respectively.

In this configuration, if the third valve 108 is in an off state, the third valve 108 outputs an output from the first valve 106 through the third output port 108c. Accordingly, in an embodiment, a pressure from the pressure unit 101a may be applied to the fluid system 10. If the first valve 106 is in an off state, a low pressure is applied to the fluid system 10, and in an on state, a high pressure is applied to the fluid system 10. Thus, in an embodiment, the state of the second valve 107 does not matter.

In an embodiment, if the third valve 108 is in an on state, the third valve 108 outputs an output from the second valve 107 to the outside via the third output port 108c. Accordingly, in this embodiment, a vacuum from the vacuum unit 101b may be applied to the fluid system 10. For example, if the second valve 107 is in an off state, high vacuum is applied to the fluid system 10, and if the second valve 107 is in an on state, low vacuum is applied to the fluid system 10. In an embodiment, whether the first valve 106 is in an on state or in an off state does not matter. As described above, various pressures and various vacuums may be selected and supplied to the fluid system 10. FIG. 3 is a table showing an example of operational states of the above-described pump and valve array 110.

In FIG. 2, the pump and valve array 110 includes only four regulators—two for pressure and two for vacuum—and three valves are illustrated. However, the above pump and valve array 110 is merely an example shown for convenience of description, and may also be designed other configurations according to the specifications of the fluid system 10. The amount of pressure and vacuum may be further subdivided, and for example, a pump and valve array having eight regulators and seven valves may be used. Also, the regulators and the valves may be arranged so as to further subdivide the amount of pressure or the amount of vacuum. In order to stop the fluid in the fluid system 10, one of the regulators may be designed to output atmospheric pressure.

FIGS. 4 and 5 are schematic views illustrating an exemplary embodiment of a method of controlling a fluid flow in the fluid system 10 using the above-described fluid control apparatus 100, wherein the fluid system 10 is in the form of an LOC. Referring to FIG. 4, the fluid system 10 has a structure in which an inlet 12, an outlet 13 and a chamber 14, where reactions may take place, are disposed on a substrate 11. In the related art, a reagent needed for reactions in the chamber 14, or a fluid such as a sample, flows simply from the inlet 12 to the outlet 13. However, when the fluid control apparatus 100 according to the current embodiment (e.g., an AVV system) is connected to the outlet 13, a fluid may be controlled to flow in both directions. Accordingly, inflow and outflow of the fluid may be controlled in any direction. In the related art, to perform control in this manner, other ports are used in addition to the inlet 12 and the outlet 13, and systems for supplying a fluid via the added ports are also desirable. Thus, when a plurality of chambers 14 are disposed in an array on the substrate 11, the interface between the fluid control apparatus and the LOC becomes more complicated.

However, by using the fluid control apparatus 100 according to an embodiment, the above-described complexity may be significantly reduced. Although the fluid control apparatus 100 is connected to the outlet 13 in FIG. 4, the fluid control apparatus 100 may alternatively be connected to the inlet 12. Also, as illustrated in FIG. 5, the fluid control apparatus 100 may be connected to both the inlet 12 and the outlet 13.

It should be understood that the exemplary embodiments described therein should be considered in a descriptive sense only and not for purposes of limitation. Descriptions of features or aspects within each embodiment should be considered as available for other similar features or aspects in other embodiments.

What is claimed is:

1. A fluid control apparatus for driving a fluid in a fluid system comprising:
   a pump and valve array configured to selectively provide pressure and vacuum of various degrees to a fluid system through a single port, which selectively provides one of a pressure or a vacuum of various degrees; wherein the pump and valve array comprises
   a pump system comprising a pressure unit, which provides an air pressure, and vacuum unit, which provides a vacuum;
   a plurality of regulators, which are separately connected to the pressure unit and the vacuum unit of the pump system and output the air pressure or the vacuum; and
   a valve system, which selects a regulator to output the air pressure or the vacuum; and
   an intermediate bin, which is connected between the pump and valve array and the fluid system, the intermediate bin comprising a reservoir unit, which stores a fluid discharged from the fluid system,
   wherein the fluid system comprises a lab-on-a-chip.

2. The fluid control apparatus of claim 1, wherein the pump system further comprises a pressure pump, which provides an air pressure, and a vacuum pump, which provides a vacuum.

3. The fluid control apparatus of claim 1, wherein the pump system provides the air pressure and the vacuum at the same time.

4. The fluid control apparatus of claim 1, wherein the plurality of regulators comprises:
   first and second regulators, which are connected to the pressure unit of the pump system and output a pressure of various degrees; and
   third and fourth regulators, which are connected to the vacuum unit of the pump system and output a vacuum of various degrees.

5. The fluid control apparatus of claim 4, wherein the valve system comprises:
   a first valve, which is connected to the first and second regulators and selects a pressure of one of the first and second regulators;
   a second valve, which is connected to the third and fourth regulators and selects a vacuum of one of the third and fourth regulators; and
   a third valve, which is connected to one of the first and second valves and selects an output of the first and second valves.

6. The fluid control apparatus of claim 5, wherein the first through third valves are solenoid valves.

7. The fluidic control apparatus of claim 1, wherein one of the plurality of regulators outputs a pressure equal to atmospheric pressure.

8. The fluid control apparatus of claim 1, wherein the intermediate bin further comprises
   a first through hole, which supplies pressure or vacuum from the pump and valve array to the reservoir unit; and
   a second through hole, which outputs the pressure or vacuum supplied to the reservoir unit to the outside.

9. The fluid control apparatus of claim 8, further comprising a first tube connected between the pump and valve array and the first through hole, and
   a second tube connected between the second through hole and the fluid system.

10. The fluid control apparatus of claim 8, wherein, if a vacuum is applied, a fluid supplied from the fluid system through the second through hole is gathered in the reservoir unit.

11. The fluid control apparatus of claim 5, wherein
    the first valve selects only a pressure of one of the first and second regulators;
    the second valve selects only a vacuum of one of the third and fourth regulators; and
    a third valve selects only one output of the first and second valves.

* * * * *